US00PP32487P2

(12) United States Plant Patent
Heuger

(10) Patent No.: US PP32,487 P2
(45) Date of Patent: Nov. 17, 2020

(54) ***HELLEBORUS* PLANT NAMED 'COSEH 7500'**

(50) Latin Name: ***Helleborus niger* X *Helleborus* x *hybridus***
Varietal Denomination: COSEH 7500

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/602,737

(22) Filed: Nov. 29, 2019

(51) Int. Cl.
*A01H 6/72* (2018.01)
*A01H 5/02* (2018.01)

(52) U.S. Cl.
USPC ..... Plt./439

(58) Field of Classification Search
USPC ..... Plt./439
CPC ..... A01H 6/72
See application file for complete search history.

*Primary Examiner* — Annette H Para
(74) *Attorney, Agent, or Firm* — C. A. Whealy

(57) ABSTRACT

A new and distinct cultivar of *Helleborus* plant named 'COSEH 7500', characterized by its upright and mounded plant habit; moderately vigorous growth habit; dark green-colored leaves; freely flowering habit; single white to light yellow green-colored flowers; and good garden performance.

2 Drawing Sheets

Figure 1:
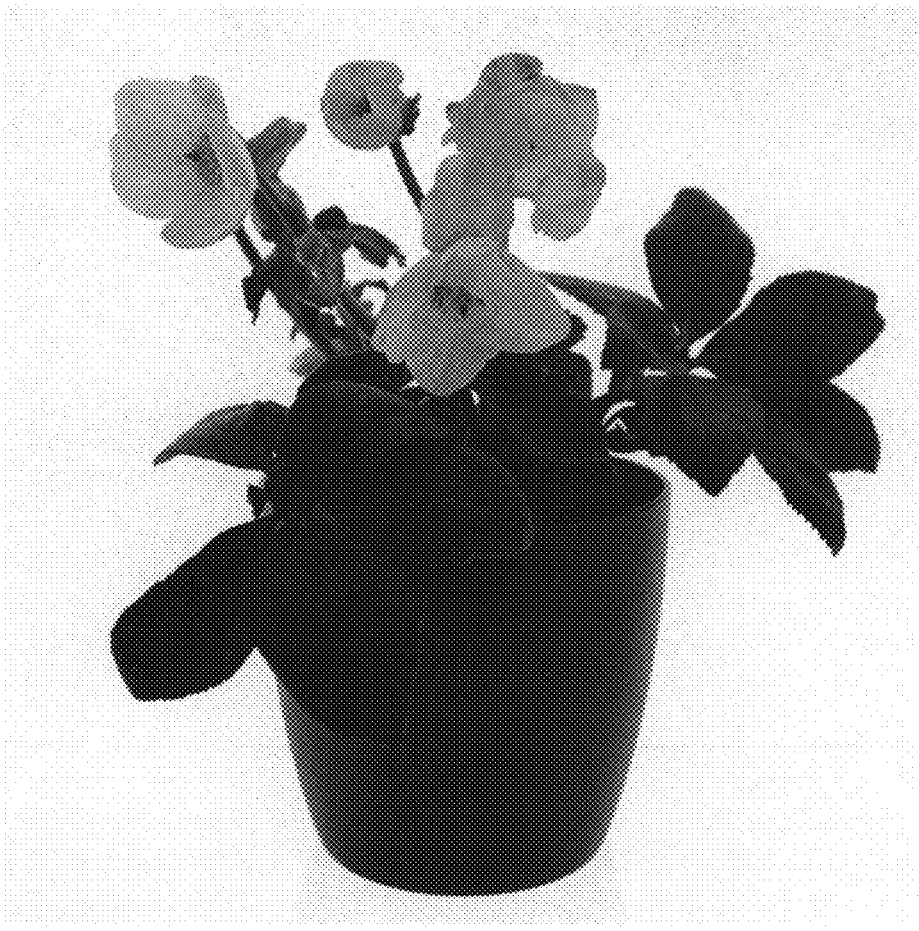

Botanical designation: *Helleborus niger* X *Helleborus* x *hybridus*.

Cultivar denomination: 'COSEH 7500'.

CROSS-REFERENCED TO CLOSELY-RELATED APPLICATIONS

Title: *Helleborus* Plant Named 'COSEH 5600'
Applicant: Josef Heuger
Plant patent application Ser. No. 16/602,791
Title: *Helleborus* Plant Named 'COSEH 5700'
Applicant: Josef Heuger
Plant patent application Ser. No. 16/602,738
Title: *Helleborus* Plant Named 'COSEH 5900'
Applicant: Josef Heuger
Plant patent application Ser. No. 16/602,735
Title: *Helleborus* Plant Named 'COSEH 6900'
Applicant: Josef Heuger
Plant patent application Ser. No. 16/602,734
Title: *Helleborus* Plant Named 'COSEH 7100'
Applicant: Josef Heuger
Filed: Concurrently with the instant application

BACKGROUND OF THE INVENTION

The present invention relates to a new and distinct cultivar of *Helleborus* plant, botanically known as *Helleborus niger* X *Helleborus* x *hybridus* and hereinafter referred to by the name 'COSEH 7500'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in October, 2011 of a unnamed selection of *Helleborus niger*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in November, 2013.

Asexual reproduction of the new *Helleborus* plant by divisions in a controlled environment in Glandorf, Germany since March, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 7500'. These characteristics in combination distinguish 'COSEH 7500' as a new and distinct *Helleborus* plant:

1. Upright and mounded plant habit.
2. Moderately vigorous growth habit.
3. Dark green-colored leaves.
4. Freely flowering habit.
5. Single white to light yellow green-colored flowers.
6. Good garden performance.

Plants of the new *Helleborus* differ from plants of the female parent selection in the following characteristics:

1. Plants of the new *Helleborus* have thicker peduncles than plants of the female parent selection.
2. Plants of the new *Helleborus* have white to light yellow green-colored flowers whereas plants of the female parent selection have pure white-colored flowers.

Plants of the new *Helleborus* differ from plants of the male parent selection in the following characteristics:

1. Plants of the new *Helleborus* have fewer leaves than plants of the male parent selection.
2. Leaves of plants of the new *Helleborus* are darker green in color than leaves of plants of the male parent selection.

Plants of the new *Helleborus* can be compared to plants of *Helleborus niger* X *Helleborus* x *hybridus* 'COSEH 5600', disclosed in a U.S. Plant Patent application filed concurrently. Plants of the new *Helleborus* differ primarily from plants of 'COSEH 5600' in flower color as plants of the new *Helleborus* have white to light yellow green-colored flowers whereas plants of 'COSEH 5600' have yellow green, white and purple-colored flowers.

Plants of the new *Helleborus* can be compared to plants of *Helleborus niger* X *Helleborus* x *hybridus* 'COSEH 5700', disclosed in a U.S. Plant Patent application filed concurrently. Plants of the new *Helleborus* differ primarily from plants of 'COSEH 5700' in flower color as plants of the new *Helleborus* have white to light yellow green-colored flowers whereas plants of 'COSEH 5700' have red purple-colored flowers.

Plants of the new *Helleborus* can be compared to plants of *Helleborus niger* X *Helleborus* x *hybridus* 'COSEH 5900', disclosed in a U.S. Plant Patent application filed concurrently. Plants of the new *Helleborus* differ primarily from plants of 'COSEH 5900' in flower color as plants of the new *Helleborus* have white to light yellow green-colored flowers whereas plants of 'COSEH 5900' have white-colored flowers. In addition, plants of the new *Helleborus* are not as vigorous as plants of 'COSEH 5900'.

Plants of the new *Helleborus* can be compared to plants of *Helleborus niger* X *Helleborus* x *hybridus* 'COSEH 6900', disclosed in a U.S. Plant Patent application filed concurrently. Plants of the new *Helleborus* differ primarily from plants of 'COSEH 6900' in flower color as plants of the new *Helleborus* have white to light yellow green-colored flowers whereas plants of 'COSEH 6900' have light yellow green-colored flowers. In addition, plants of the new *Helleborus* are not as vigorous as plants of 'COSEH 6900'.

Plants of the new *Helleborus* can be compared to plants of *Helleborus niger* X *Helleborus* x *hybridus* 'COSEH 7100', disclosed in a U.S. Plant Patent application filed concurrently. Plants of the new *Helleborus* differ primarily from plants of 'COSEH 7100' in flower color as plants of the new *Helleborus* have white to light yellow green-colored flowers whereas plants of 'COSEH 7100' have red purple-colored flowers.

Plants of the new *Helleborus* can also be compared to plants of *Helleborus niger* X *Helleborus* x *hybridus* 'LEM 100', disclosed in U.S. Plant Pat. No. 25,646. In side-by-side comparisons, plants of the new *Helleborus* differ primarily from plants of 'LEM 100' in the following characteristics:

1. Leaves of plants of the new *Helleborus* are lighter green in color than leaves of plants of 'LEM 100'.
2. Plants of the new *Helleborus* have white to light yellow green-colored flowers whereas plants of 'LEM 100' have red purple-colored flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 7500' grown in a container.

Figure 2:
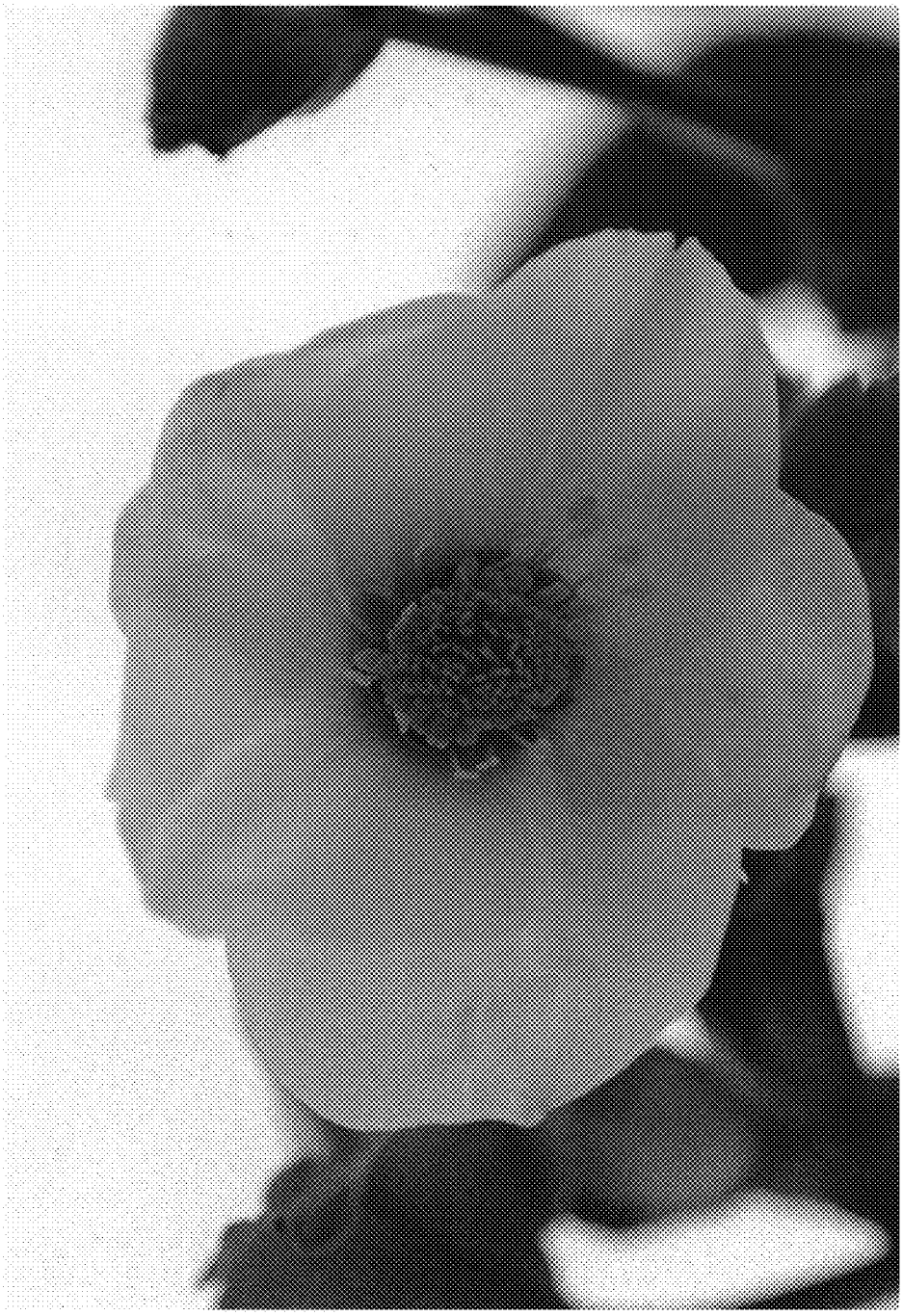

The photograph on the second sheet (FIG. 2 of 2) is a close-up view of a typical flower and leaves of 'COSEH 7500'.

DETAILED BOTANICAL DESCRIPTION

The aforementioned photographs and following observations, measurements and values describe plants grown during December in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'COSEH 7500'.

Parentage:

*Female, or seed, parent.*—Unnamed selection of *Helleborus niger*, not patented.

*Male, or pollen, parent.*—Unnamed selection of *Helleborus* x *hybridus*, not patented.

Propagation:

*Type.*—In vitro axillary meristem culture.

*Time to initiate roots, winter.*—About 55 days at temperatures about 12° C.

*Time to produce a rooted young plant, winter.*—About 170 days at temperatures ranging from 4° C. to 15° C.

*Root description.*—Thick to thin, fleshy; typically white to brown in color, actual color of the roots is dependent on substrate composition, water quality, fertilizer type and formulation, substrate temperature and physiological age of roots.

*Rooting habit.*—Low branching; sparse.

Plant description:

*Plant and growth habit.*—Herbaceous perennial; upright and mounding plant habit with flowers held within and above the foliar plane; plant shape, roughly flattened globular; moderately vigorous growth habit and moderate growth rate.

*Plant height, soil level to top of foliar plane.*—About 18.8 cm.

*Plant height, soil level to top of flowers.*—About 23.2 cm.

*Plant diameter* (*area of spread*).—About 30.7 cm.

Leaf description:

*Arrangement.*—Leaves arranged in a basal rosette; leaves palmately compound with typically seven leaflets per leaf.

*Leaf length.*—About 15.6 cm.

*Leaf width.*—About 17.7 cm.

*Leaflet length.*—About 9.3 cm.

*Leaflet width.*—About 5.3 cm.

*Leaf shape.*—Palmate; reniform in outline.

*Leaflet shape.*—Obovate to broadly obovate.

*Leaflet apex*.—Broadly acute.

*Leaflet base*.—Attenuate.

*Leaflet margin*.—Serrate; slightly undulate.

*Leaflet texture and luster, upper surface*.—Smooth, glabrous; leathery; slightly to moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to NN137A; midvein proximally, close to N186C. Developing leaflets, lower surface: Close to 147B; midvein, close to 183A. Fully developed leaflets, upper surface: Darker than between NN137A and 147A; venation, close to 147B. Fully developed leaflets, lower surface: Close to 144B to 144C and proximally tinged with close to 183A to 183B; venation, close to 144B.

*Petioles*.—Length: About 11.7 cm. Diameter: About 6 mm to 7 mm. Strength: Strong. Texture and luster, upper and lower surfaces: Smooth, glabrous; slightly glossy. Color, upper and lower surfaces: Close to 144A and slightly to heavily covered with fine dots, close to 200B.

Flower description:

*Flower shape and habit*.—Single rotate flowers; flowers slightly cupped; arranged solitary; freely flowering habit with about 25 flowers developing per plant; flowers face mostly outwardly to slightly nodding.

*Fragrance*.—None detected.

*Natural flowering season*.—Plants begin flowering about ten months after planting; plants flower from the late autumn into the winter in Germany.

*Flower longevity on the plant*.—About three to four months; sepals persistent, other flower parts are not persistent.

*Flower buds*.—Length: About 2.5 cm. Diameter: About 1.5 cm. Shape: Ovate. Texture and luster: Smooth, glabrous; matte. Color: Close to 145C and proximally, close to 145B.

*Inflorescence height*.—About 8 cm.

*Inflorescence diameter*.—About 10.1 cm.

*Flower diameter*.—About 7.6 cm by 7.6 cm.

*Flower depth* (*height*).—About 3 cm.

*Petals*.—All petals are transformed into nectaries.

*Sepals*.—Quantity and arrangement: About five, arranged in a single whorl. Length: About 4.4 cm. Width: About 4.2 cm. Shape: Broadly ovate, slightly to moderately concave. Apex: Obtuse. Base: Truncate to rounded. Margin: Entire; not undulate. Texture and luster, upper surface: Smooth, glabrous; matte. Texture and luster, lower surface: Smooth, glabrous; very slightly glossy. Color: When opening, upper surface: Close to NN155C and proximally, close to 145B; venation, similar to lamina. When opening, lower surface: Close to 155C and proximally, close to 145B; venation, similar to lamina. Fully opened, upper surface: Close to NN155C and proximally, close to 145B; venation, similar to lamina; with development, color becoming closer to 145B. Fully opened, lower surface: Close to 155C and proximally, close to 145B; venation, similar to lamina; with development, color becoming closer to 145B.

*Flower bracts*.—Quantity per flower: Typically one or two. Length: About 6.4 cm. Width: About 4 cm. Shape: Broadly ovate. Apex: Acute. Base: Truncate. Margin: Finely serrate to serrate; slightly undulate. Color, upper surface: Close to 137A; venation, similar to lamina. Color, lower surface: Close to 147B to 147C; venation, close to 183A.

*Peduncles*.—Length: About 16 cm. Diameter: About 8 mm to 11 mm. Aspect: About 20° from vertical. Strength: Strong. Texture and luster: Smooth, glabrous; moderately glossy. Color: Close to 144A and moderately to heavily covered with fine dots, close to 183B.

*Pedicels*.—Length: About 4.6 cm. Diameter: About 3 mm to 4 mm. Aspect: About 12.5° from peduncle axis. Strength: Moderately strong. Texture and luster: Smooth, glabrous; moderately glossy. Color: Close to 144B and moderately to heavily covered with fine dots, close to 183B.

*Reproductive organs*.—Stamens: Quantity per flower: About 100. Filament length: About 1.6 cm. Filament color: Close to NN155D. Anther shape: Double and broadly reniform; basifixed. Anther size: About 2 mm by 2 mm. Anther color: Close to 150C. Pollen amount: Moderate. Pollen color: Close to 4D. Pistils: Quantity per flower: About six to twelve. Pistil length: About 7 mm. Stigma diameter: About 0.3 mm. Stigma shape: Club-shaped. Stigma color: Close to 150D. Style length: About 6.5 mm. Style color: Close to 60C. Ovary color: Close to between 145D and 150D. Nectaries (transformed petals): Quantity per flower: About 16. Length: About 1.3 cm. Diameter: About 4.5 mm. Shape: Tubular, flattened. Texture and luster, inner and outer surfaces: Smooth, glabrous; slightly glossy. Color, immature, inner and outer surfaces: Close to 144C, distally, close to N144B and proximally, close to 146C and 146D. Color, mature, inner and outer surfaces: Close to 144C, distally, close to 154A and proximally, close to 153B; with development, close to 144A to 144B, distally, close to 154A and proximally, close to 153B.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 7500' as illustrated and described.

* * * * *